United States Patent
Kasper et al.

(10) Patent No.: US 9,625,473 B2
(45) Date of Patent: Apr. 18, 2017

(54) CYTOKINE BIOMARKERS AS PREDICTIVE BIOMARKERS OF CLINICAL RESPONSE FOR GLATIRAMER ACETATE

(71) Applicants: Lloyd H. Kasper, Norwhich, VT (US); Jacqueline Y. Smith, Lebanon, NH (US)

(72) Inventors: Lloyd H. Kasper, Norwhich, VT (US); Jacqueline Y. Smith, Lebanon, NH (US)

(73) Assignee: TEVA PHARMACEUTICAL INDUSTRIES LTD., Petach-Tikva (IL)

(*) Notice: Subject to any disclaimer, the term of this patent is extended or adjusted under 35 U.S.C. 154(b) by 0 days.

(21) Appl. No.: 14/706,843

(22) Filed: May 7, 2015

(65) Prior Publication Data
US 2015/0241446 A1  Aug. 27, 2015

Related U.S. Application Data

(62) Division of application No. 14/250,955, filed on Apr. 11, 2014, now Pat. No. 9,063,153, which is a division of application No. 13/269,913, filed on Oct. 10, 2011, now Pat. No. 8,709,433.

(60) Provisional application No. 61/391,968, filed on Oct. 11, 2010.

(51) Int. Cl.
| G01N 33/68 | (2006.01) |
| A61K 38/07 | (2006.01) |
| C07K 14/52 | (2006.01) |
| A61K 9/00 | (2006.01) |
| A61K 31/785 | (2006.01) |

(52) U.S. Cl.
CPC ....... *G01N 33/6863* (2013.01); *A61K 9/0019* (2013.01); *A61K 31/785* (2013.01); *A61K 38/07* (2013.01); *C07K 14/52* (2013.01); *G01N 33/6866* (2013.01); *G01N 33/6869* (2013.01); *G01N 33/6896* (2013.01); *G01N 2333/525* (2013.01); *G01N 2333/54* (2013.01); *G01N 2333/55* (2013.01); *G01N 2333/57* (2013.01); *G01N 2800/285* (2013.01); *G01N 2800/52* (2013.01)

(58) Field of Classification Search
None
See application file for complete search history.

(56) References Cited

U.S. PATENT DOCUMENTS

| 3,849,550 | A | 11/1974 | Teitelbaum et al. |
| 5,800,808 | A | 9/1998 | Konfino et al. |
| 5,981,589 | A | 11/1999 | Konfino et al. |
| 6,048,898 | A | 4/2000 | Konfino et al. |
| 6,054,430 | A | 4/2000 | Konfino et al. |
| 6,214,791 | B1 | 4/2001 | Arnon et al. |
| 6,342,476 | B1 | 1/2002 | Konfino et al. |
| 6,362,161 | B1 | 3/2002 | Konfino et al. |
| 6,514,938 | B1 | 2/2003 | Gad et al. |
| 6,620,847 | B2 | 9/2003 | Konfino et al. |
| 6,800,285 | B2 | 10/2004 | Rodriguez et al. |
| 6,800,287 | B2 | 10/2004 | Gad et al. |
| 6,844,314 | B2 | 1/2005 | Eisenbach-Schwartz et al. |
| 6,939,539 | B2 | 9/2005 | Konfino et al. |
| 7,022,663 | B2 | 4/2006 | Gilbert et al. |
| 7,033,582 | B2 | 4/2006 | Yong et al. |
| 7,074,580 | B2 | 7/2006 | Gad et al. |
| 7,163,802 | B2 | 1/2007 | Gad et al. |
| 7,199,098 | B2 | 4/2007 | Konfino et al. |
| 7,279,172 | B2 | 10/2007 | Aharoni |
| 7,351,686 | B2 | 4/2008 | Eisenbach-Schwartz et al. |
| 7,407,936 | B2 | 8/2008 | Eisenbach-Schwartz et al. |
| 7,425,332 | B2 | 9/2008 | Aharoni et al. |
| 7,429,374 | B2 | 9/2008 | Klinger |
| 7,495,072 | B2 | 2/2009 | Dolitzky et al. |
| 7,560,100 | B2 | 7/2009 | Pinchasi et al. |
| 7,566,767 | B2 | 7/2009 | Strominger et al. |
| 7,615,359 | B2 | 11/2009 | Gad et al. |

(Continued)

FOREIGN PATENT DOCUMENTS

| WO | WO 95/31990 | 11/1995 |
| WO | WO 98/30227 | 7/1998 |

(Continued)

OTHER PUBLICATIONS

Valenzuela et al., Clinical response to glatiramer acetate correlates with modulation of IFN-gama and IL-4 expression in multiple sclerosis, Jul. 2007, Multiple Sclerosis 13(6):754-762.*
Nov. 27, 2015 First Examination Report issued by the Australian Patent Office in connection with Australian Patent Application No. 201131842.
Apr. 2, 2015 Official Action issued by the Eurasian Patent Office in connection with Eurasian Patent Application No. 201390543 (including English language translation).
Aug. 3, 2015 Response to Apr. 2, 2015 Official Action filed wlth the Eurasian Patent Office in connection with Eurasian Patent Application No. 201390543.
Nov. 26, 2016 Official Action issued by the Eurasian Patent Office in connection with Eurasian Patent Application No. 201390543.
Mar. 25, 2016 Response to Nov. 26, 2016 Official Action filed with the Eurasian Patent Office in connection with Eurasian Patent Application No. 201390543.

(Continued)

*Primary Examiner* — John Ulm
(74) *Attorney, Agent, or Firm* — John P. White; Gary J. Gershik; Cooper & Dunham LLP (57) ABSTRACT

A method for treating a human subject afflicted with multiple sclerosis or a single clinical attack consistent with multiple sclerosis with a pharmaceutical composition comprising glatiramer acetate and a pharmaceutically acceptable carrier, comprising the steps of determining whether the human subject is a glatiramer acetate responder by evaluating a biomarker selected from the group consisting of IL-17 concentration, TNF-α concentration, IL-2 concentration and IFN-γ concentration, or a combination thereof, in the blood of the human subject and administering the pharmaceutical composition comprising glatiramer acetate and a pharmaceutically acceptable carrier to the human subject only if the human subject is identified as a glatiramer acetate responder.

19 Claims, 4 Drawing Sheets

(56) References Cited

U.S. PATENT DOCUMENTS

| | | |
|---|---|---|
| 7,625,861 B2 | 12/2009 | Konfino et al. |
| 7,855,176 B1 | 12/2010 | Altman et al. |
| 7,923,215 B2 | 4/2011 | Klinger |
| 7,968,511 B2 | 6/2011 | Vollmer et al. |
| 8,232,250 B2 | 7/2012 | Klinger |
| 8,367,605 B2 | 2/2013 | Konfino et al. |
| 8,389,228 B2 | 3/2013 | Klinger |
| 8,399,211 B2 | 3/2013 | Gad et al. |
| 8,399,413 B2 | 3/2013 | Klinger |
| 8,709,433 B2 | 4/2014 | Kasper |
| 8,759,302 B2 | 6/2014 | Dhib-Jalbut |
| 8,815,511 B2 | 8/2014 | Tchelet et al. |
| 8,920,373 B2 | 12/2014 | Altman et al. |
| 8,969,302 B2 | 3/2015 | Klinger |
| 9,018,170 B2 | 4/2015 | Altman et al. |
| 9,063,153 B2 | 6/2015 | Kasper |
| 9,155,775 B1 | 10/2015 | Cohen et al. |
| 9,155,776 B2 | 10/2015 | Klinger |
| 2002/0037848 A1 | 3/2002 | Eisenbach-Schwartz |
| 2002/0077278 A1 | 6/2002 | Yong et al. |
| 2003/0170729 A1 | 9/2003 | Klinger |
| 2005/0019322 A1 | 1/2005 | Rodriguez et al. |
| 2005/0170004 A1 | 8/2005 | Rosenberger |
| 2006/0052586 A1 | 3/2006 | Dolitzky |
| 2006/0172942 A1 | 8/2006 | Dolitzky |
| 2006/0240463 A1 | 10/2006 | Lancet |
| 2006/0264354 A1 | 11/2006 | Aharoni et al. |
| 2007/0021324 A1 | 1/2007 | Dolitzky |
| 2007/0021341 A1 | 1/2007 | Sela et al. |
| 2007/0037740 A1 | 2/2007 | Pinchasi et al. |
| 2007/0048794 A1 | 3/2007 | Gad et al. |
| 2007/0054857 A1 | 3/2007 | Pinchasi et al. |
| 2007/0059798 A1 | 3/2007 | Gad |
| 2007/0161566 A1 | 7/2007 | Pinchasi |
| 2007/0173442 A1 | 7/2007 | Vollmer |
| 2007/0244056 A1 | 10/2007 | Hayardeny et al. |
| 2007/0248569 A1 | 10/2007 | Eisenbach-Schwartz |
| 2008/0085269 A1 | 4/2008 | Eisenbach-Schwartz |
| 2008/0118553 A1 | 5/2008 | Frenkel et al. |
| 2008/0207526 A1 | 8/2008 | Strominger |
| 2008/0261894 A1 | 10/2008 | Kreitman et al. |
| 2009/0048181 A1 | 2/2009 | Schipper et al. |
| 2009/0053253 A1 | 2/2009 | Klinger |
| 2009/0149541 A1 | 6/2009 | Stark et al. |
| 2009/0214470 A1 | 8/2009 | Eisenbach-Schwartz et al. |
| 2010/0167983 A1 | 7/2010 | Kreitman et al. |
| 2010/0210817 A1 | 8/2010 | Gad et al. |
| 2010/0285600 A1 | 11/2010 | Lancet et al. |
| 2010/0298227 A1 | 11/2010 | Aharoni et al. |
| 2010/0305023 A1 | 12/2010 | Stark et al. |
| 2011/0046065 A1 | 2/2011 | Klinger |
| 2011/0060279 A1 | 3/2011 | Altman et al. |
| 2011/0066112 A1 | 3/2011 | Altman |
| 2011/0117115 A1 | 5/2011 | Eisenbach-Schwartz |
| 2012/0027718 A1 | 2/2012 | Kreitman et al. |
| 2012/0121619 A1 | 5/2012 | Kasper |
| 2012/0309671 A1 | 12/2012 | Klinger |
| 2014/0107208 A1 | 4/2014 | Comabella et al. |
| 2014/0193827 A1 | 7/2014 | Schwartz et al. |
| 2014/0271532 A1 | 9/2014 | Kreitman et al. |
| 2014/0271630 A1 | 9/2014 | Vollmer |
| 2014/0294899 A1 | 10/2014 | Kasper et al. |
| 2014/0322158 A1 | 10/2014 | Dhib-Jalbut |
| 2015/0045306 A1 | 2/2015 | Tchelet et al. |
| 2015/0110733 A1 | 4/2015 | Tchelet et al. |
| 2015/0164977 A1 | 6/2015 | Klinger |
| 2015/0202247 A1 | 7/2015 | Klinger |

FOREIGN PATENT DOCUMENTS

| | | |
|---|---|---|
| WO | WO 00/05250 | 2/2000 |
| WO | WO 00/05249 | 3/2000 |
| WO | WO 00/18794 | 4/2000 |
| WO | WO 00/20010 | 4/2000 |
| WO | WO 00/27417 | 5/2000 |
| WO | WO 01/60392 | 8/2001 |
| WO | WO 01/93828 | 12/2001 |
| WO | WO 01/97846 | 12/2001 |
| WO | WO 03/048735 | 6/2003 |
| WO | WO 2004/103297 | 2/2004 |
| WO | WO 2004/043995 | 5/2004 |
| WO | WO 2004/064717 | 8/2004 |
| WO | WO 2004/091573 | 10/2004 |
| WO | WO 2005/041933 | 5/2005 |
| WO | WO 2005/084377 | 9/2005 |
| WO | WO 2006/029036 | 3/2006 |
| WO | WO 2006/029393 | 3/2006 |
| WO | WO 2006/029411 | 3/2006 |
| WO | WO 2006/050122 | 5/2006 |
| WO | WO 2006/083608 | 8/2006 |
| WO | WO 2006/089164 | 8/2006 |
| WO | WO 2006/116602 | 11/2006 |
| WO | WO 2007/030573 | 3/2007 |
| WO | WO 2007/081975 | 7/2007 |
| WO | WO 2008/006026 | 1/2008 |
| WO | WO 2009/070298 | 6/2009 |
| WO | WO 2011/008274 | 1/2011 |
| WO | WO 2011/022063 | 2/2011 |
| WO | WO 2012/051106 | 4/2012 |
| WO | WO 2013/055683 | 4/2013 |
| WO | WO 2014/058976 | 4/2014 |
| WO | WO 2014/100639 | 6/2014 |
| WO | WO 2014/100643 | 6/2014 |
| WO | WO 2014/107533 | 7/2014 |
| WO | WO 2014/165280 | 10/2014 |
| WO | WO 2015/061367 | 4/2015 |

OTHER PUBLICATIONS

Aug. 24, 2015 Communication Pursuant to Article 94(3) EPC issued by the European Patent Office in connection with European Patent Application No. 11833199.0.

Nov. 12, 2015 Response to Aug. 24, 2015 Communication Pursuant to Article 94(3) EPC filed with the European Patent Office in connection with European Patent Application No. 11833199.0

Feb. 4, 2016 Result of Consultation issued by the European Patent Office in connection with European Patent Application No. 11833199.0.

Feb. 25, 2016 Response to Feb. 4, 2016 Result of Consultation filed with the European Patent Office in connection with European Patent Application No. 11833199.0.

Jul. 7, 2015 Office Action issued by the Japanese Patent Office in connection with Japanese Patent Application No. 2013-533913 (including English language translation).

Oct. 7, 2015 Response to Jul. 7, 2015 Office Action filed with the Japanese Patent Office in connection with Japanese Patent Application No. 2013-533913.

Jan. 5, 2016 Decision of Rejection issued by the Japanese Patent Office in connection with Japanese Patent Application No. 2013-533913 (including English language translation).

Jun. 23, 2015 Response to Dec. 23, 2014 Further Examination Report filed with the New Zealand Patent Office in connection with New Zealand Patent Application No. 609938.

Jul. 15, 2015 Further Examination Report issued by the New Zealand Patent Office in connection with New Zealand Patent Application No. 6099398.

Oct. 2, 2015 Response to Jul. 15, 2015 Further Examination Report filed with the New Zealand Patent Office in connection with New Zealand Patent Application No. 609938.

Oct. 22, 2015 Further Examination Report issued by the New Zealand Patent Office in connection with New Zealand Patent Application No. 609938.

Oct. 30, 2015 Response to Oct. 22, 2015 Further Examination Report filed with the New Zealand Patent Office in connection with New Zealand Patent Application No. 609938.

Apr. 20, 2016 Response to Dec. 23, 2014 First Examination Report filed with the New Zealand Patent Office in connection with New Zealand Patent Application No. 703122.

Blanco et al. 'Effect of glatiramer acetate (Copaxone®) on the immunophenotypic and cytokine profile and BDNF production in multiple sclerosis: A longitudinal study,' Neuroscience Letters, (2006), vol. 406, pp. 270-275.

(56) References Cited

OTHER PUBLICATIONS

Charach et al. "Development of Crohn's Disease in a Patient with Multiple Sclerosis Treated with Copaxone" (2008) vol. 77, pp. 198-200.
Valenzuela M, et al. 'IL-27 Mediates Glatiramer Acetate Effect on Antigen Presenting Cells in Multiple Sclerosis,' Nuerology, (2010) vol. 74, suppl 2 p. A166.
Oct. 15, 2007 Office Action in connection with U.S. Appl. No. 11/409,590.
Jan. 15, 2008 Amendment in Response to Oct. 15, 2007 Office Action in connection with U.S. Appl. No. 11/409,590.
Mar. 14, 2008 Supplemental Response to Oct. 15, 2007 Office Action in connection with U.S. Appl. No. 11/409,590.
Jun. 18, 2008 Office Communication in connection with U.S. Appl. No. 11/409,590.
Jul. 18, 2008 Response to Jun. 18, 2008 Office Communication in connection with U.S. Appl. No. 11/409,590.
Oct. 24, 2008 Office Action in connection with U.S. Appl. No. 11/409,590.
Apr. 24, 2009 Amendment in Response to Oct. 24, 2008 Office Action in connection with U.S. Appl. No. 11/409,590.
Aug. 20, 2009 Final Office Action in connection with U.S. Appl. No. 11/409,590.
U.S. Appl. No. 11/590,338, filed Oct. 30, 2006 (Pinchasi et al.).
Office Action issued Jan. 4, 2013 in connection with U.S. Appl. No. 13/269,913, filed Oct. 10, 2011.
Response to Office Action issued Jan. 4, 2013, filed Feb. 4, 2013 in connection with U.S. Appl. No. 13/269,913, filed Oct. 10, 2011.
Office Action issued Mar. 26, 2013 in connection with U.S. Appl. No. 13/269,913, filed Oct. 10, 2011.
Response to Office Action issued Mar. 26, 2013, filed Jul. 24, 2013 in connection with U.S. Appl. No. 13/269,913, filed Oct. 10, 2011.
Office Action issued Sep. 20, 2013 in connection with U.S. Appl. No. 13/269,913, filed Oct. 10, 2011.
Response to Office Action issued Sep. 20, 2013, filed Nov. 27, 2013 in connection with U.S. Appl. No. 13/269,913, filed Oct. 10, 2011.
Notice of Allowance issued Dec. 11, 2013 in connection with U.S. Appl. No. 13/269,913, filed Oct. 10, 2011.
U.S. Appl. No. 14/630,326, filed Feb. 24, 2015, Klinger.
U.S. Appl. No. 14/673,257, filed Mar. 30, 2015, Klinger.
Mar. 2, 2012 Office Action Issued in Connection With U.S. Appl. No. 13/049,720, filed Mar. 16, 2011 (Dhib-Jalbut).
Apr. 2, 2012 Amendment filed in Connection With U.S. Appl. No. 13/049,720, filed Mar. 16, 2011 (Dhib-Jalbut).
May 16, 2012 Office Action Issued in Connection With U.S. Appl. No. 13/049,720, filed Mar. 16, 2011 (Dhib-Jalbut).
Aug. 16, 2012 Amendment filed in Connection With U.S. Appl. No. 13/049,720, filed Mar. 16, 2011 (Dhib-Jalbut).
Aug. 30, 2012 Office Action Issued in Connection With U.S. Appl. No. 13/049,720, filed Mar. 16, 2011.
Feb. 27, 2013 Amendment filed in Connection With U.S. Appl. No. 13/049,720, filed Mar. 16, 2011.
Mar. 1, 2013 Office Action Issued in Connection With U.S. Appl. No. 13/049,720, filed Mar. 16, 2011.
Mar. 19, 2013 Response in Connection With U.S. Appl. No. 13/049,720, filed Mar. 16, 2011 (Dhib-Jalbut).
Mar. 26, 2013 Office Action Issued in Connection With U.S. Appl. No. 13/049,720, filed Mar. 16, 2011 (Dhib-Jalbut).
Jan. 10, 2014 Office Action Issued in Connection With U.S. Appl. No. 13/049,720, filed Mar. 16, 2011 (Dhib-Jalbut).
Jan. 24, 2014 Amendment filed in Connection With U.S. Appl. No. 13/049,720, filed Mar. 16, 2011 (Dhib-Jalbut).
Jan. 27, 2011 Supplemental Response to Jan. 9, 2014 examiner initiated interview in Connection With U.S. Appl. No. 13/049,720, filed Mar. 16, 2011 (Dhib-Jalbut).
Notice of Allowance issued Jan. 31, 2014 in Connection With U.S. Appl. No. 13/049,720, filed Mar. 16, 2011 (Dhib-Jalbut).
Office Action issued Jul. 10, 2014 in connection with U.S. Appl. No. 14/250,955, filed Apr. 11, 2014.

Response to Office Action issued Jul. 10, 2014, filed Oct. 10, 2014 in connection with U.S. Appl. No. 14/250,955, filed Apr. 11, 2014.
Office Action issued Dec. 4, 2014 in connection with U.S. Appl. No. 14/250,955, filed Apr. 11, 2014.
Response to Office Action issued Dec. 4, 2014, filed Dec. 10, 2014 in connection with U.S. Appl. No. 14/250,955, filed Apr. 11, 2014.
PCT International Search Report Issued Apr. 19, 2012 for International Application Publication WO 2012/051106.
PCT International Preliminary Report on Patentability issued Apr. 16, 2013 for International Application WO 2012/051106.
Apr. 2, 2014 Office Action issued in connection with European Patent Application No. 11833199.0.
Response to Apr. 2, 2014 Office Action, filed Jul. 30, 2014 in connection with European Patent Application No. 11833199.0.
Sep. 24, 2014 Office Action issued in connection with European Patent Application No. 11833199.0.
Response to Sep. 24, 2014 Office Action, filed Jan. 23, 2015 in connection with European Patent Application No. 11833199.0.
Sep. 17, 2013 First Examination Report issued in connection with New Zealand Application No. 609938.
Response to Sep. 17, 2013 First Examination Report, filed Dec. 17, 2014 in connection with New Zealand Application No. 609938.
Dec. 23, 2014 Further Examination Report issued in connection with New Zealand Application No. 609938.
Dec. 23, 2014 First Examination Report issued in connection with New Zealand Application No. 703122.
International Search Report issued Apr. 4, 2014 in connection with PCT International Application No. WO2014/058976, filed Oct. 9, 2013 (Comabella et al.).
Written Opinion of the International Searching Authority issued Apr. 4, 2014 in connection with PCT International Application No. WO2014/058976, filed Oct. 9, 2013 (Comabella et al.).
Notice of Allowance issued Feb. 6, 2015 in connection with U.S. Appl. No. 14/250,955, filed Apr. 11, 2014.
Canadian Patent Application No. 2,606,194, filed Apr. 24, 2006 (Lancet et al.), Canadian counterpart of U.S. Appl. No. 11/409,590.
European Patent Application No. 06758673.5, filed Apr. 24, 2006 (European counterpart of U.S. Appl. No. 11/409,590).
PCT International Preliminary Report on Patentability issued Mar. 19, 2009 for International Application No. PCT/US2006/016036 (WO 2006/116602) (International counterpart of U.S. Appl. No. 11/409,509).
PCT International Search Report Issued Aug. 11, 2008 for International Application No. PCT/US2006/016036 (WO 2006/116602) (International counterpart of U.S. Appl. No. 11/409,509).
PCT Written Opinion issued Aug. 11, 2008 for International Application No. PCT/US2006/016036 (WO 2006/116602) (International counterpart of U.S. Appl. No. 11/409,509).
Feb. 18, 2010 Extended European Search Report in connection with European Patent Application No. 06758673.5.
Opposition filed on Feb. 15, 2010 in connection with European Patent No. 1 459 065, granted Jul. 28, 2010 (European Application No. 02790028.1).
Opposition filed on Apr. 28, 2011 in connection with European Patent No. 1 115 743, granted May 26, 2009.
Opposition filed on Oct. 5, 2010 in connection with European Patent No. 1799703, granted Jan. 6, 2010.
Aharoni "Glatiramer acetate-specific T cells in the brain express T helper 2/3 cytokines and brain-derived neurotrophic factor in situ." PNAS Aug. 2003;100(24):14157-62.
Anderson, et al., (1992) "Revised estimate of the prevalence of multiple sclerosis in the United States." Ann Neurol., 31: 333-336.
Aranami et al. "Th17 Cells and autoimmune encephalomyelitis (EAE/MS)". Allergol Int. Jun. 2008; 57(2):115-20.
Beebe et al., "The role of IL-10 in autoimmune disease: systemic lupus erythematosus (SLE) and multiple sclerosis (MS)," Cytokine Growth factor rev. 12 (2002):403-412.
Begum-Haque et al., "Downregulation of IL-17 and IL-6 in the central nervous system by glatiramer acetate in experimental autoimmune encephalomyelitis." J Neuroimmunol. Nov. 15, 2008;204(1-2):58-65.

(56) References Cited

OTHER PUBLICATIONS

Bornstein, et al., "Treatments of Multiple Sclerosis with a Synthetic Polypeptide: Preliminary Results," Ann. Neurol., 1980, 8, 117 (Abstract).
Bornstein, et al., "Treatments of Multiple Sclerosis with a Synthetic Polypeptide: Preliminary Results," Trans. Am. Neurol. Assoc., 1980, 105, 348-350.
Bornstein, et al., "Multiple Sclerosis: Trial of a Synthetic Polypeptide," Ann. Neurol., 1982, 11, 317-319.
Bornstein, et al., "Clinical Trials of Copolymer 1 in Multiple Sclerosis," Ann. N.Y. Acad. Sci. (USA), 1984, 366-372.
Bornstein, et al., "Clinical Trials of a Synthetic Polypeptide (Copolymer 1) for the treatment of Mutliple Sclerosis" in Gonsett et al., Immunological and Clinical Aspects of Multiple Sclerosis (MTP Press, The Hague, 1984) 144-150.
Bornstein, et al., "Multiple Sclerosis: Clinical Trials of a Synthetic Polypeptide, Copolymer 1," Neurol., 1985, 35, (Suppl. 1), 103 (Abstract).
Bornstein, "Cop 1 may be Beneficial for Patients with Exacerbating-remitting Form of Multiple Sclerosis," Adv. Ther. (USA), 1987, 4, 206 (Abstract) (Exhibit 45).
Bornstein, et al., "A Pilot Trial of Cop 1 in Exacerbating-remitting Multiple Sclerosis," New Eng. J. Med., 1987, 317(7), 408-414.
Bornstein, et al., "Clinical Experience with COP-1 in Multiple Sclerosis," Neurol., 1988, 38(Suppl. 2) 66-69.
Bornstein et al., "Rationale for Immunomodulating Therapies of Multiple Sclerosis: Clinical Trial Design in Multiple Sclerosis Therapy," Neurol., 1988, vol. 38 (Suppl.2), pp. 80-81 [R].
Bornstein, et al., "Pilot Trial of COP-1 in Chronic Progressive Multiple Sclerosis: Preliminary Report," from The International Multiple Sclerosis Conference: An Update on Multiple Sclerosis, Roma (Italy), Sep. 15-17, 1988, in Elsevier Science Publisher, 1989, 225-232.
Bornstein, et. al., "Clinical Trials of Cop 1 in Multiple Sclerosis," in Handbook of Multiple Sclerosis (S.D. Cook Marcel Rekker, ed., 1990) 469-480.
Bornstein , et al., "A Placebo-controlled, Double-blind, Randomized Two-center, Pilot Trial of Cop 1 in Chronic Prgressive Multiple Sclerosis," Neurol., 1991, 41, 533-539.
Bornstein, et al., "Treatment of Multiple Sclerosis with Copolymer 1" in Treatment of Multiple Sclerosis: Trial Design, Results and Future Perspectives (Rudick R.A. & Goodkin D.E., eds., Springer Lerlag, London, 1992) 173-198.
Bornstein, "Clincal Experience: Hopeful Prospects in Multiple Sclerosis," Hospital Practice (Off. Ed.), 1992, vol. 27, No. 5, pp. L135-L158, 141-142, 145-158.
Brex et al., (2002) "A longitudinal study of abnormalities on MRI and disability from multiple sclerosis" Engl. J. Med., 3: 158-64.
Burger, Daniella et al., "Glatiramer acetate increases IL-1 receptor antagonist but decreases T cell-induced IL-B in human monocytes and multiple sclerosis," PNAS PNAS 2009 106 (11) 4355-4359 (2009); Early Edition 0812183106.
Cagguila et al., "Neurotrophic factors and clinical recovery in RR-MS," Scand J Immunol 2005, 62: 176-82.
Chen et al., "Glatiramer acetate induces a Th-2 biased response and cross-reactivity with myelin basic protein in patients with MS." Multiple Sclerosis 2001; 7:209-219.
Cohen et al., Identifying and treating patients with suboptimal responses. Neurology Dec. 28, 2004;63(12 Suppl 6):S33-40.
Comi G. et al., (2001) "European/Canadian Multicenter, Double-Blind, Randomized, Placebo-controlled study of the effects of Glatiramer acetate on Magnetic resonance imaging-measured disease activity and burden in patients with relapsing multiple sclerosis" Ann. Neurol. 49:290-297.
Comi, et al. (2008) "Results from a phase III, one-year, randomized, double-blind, parallel-group, dose-comparison study with glatiramer acetate in relapsing-remitting multiple sclerosis". Mult Scler., 14(Suppl 1):S299.

Comi et al. Treatment with glatiramer acetate delays conversion to clinically definite multiple sclerosis (CDMS) in patients with clinically isolated syndromes (CIS). Neurology 2008; 71 (2): 153.
Cua et al., "Transgenic Interleukin-10 prevents induction of experimental autoimmune encephalomyelitis." J. Exp. Med. 189 (1999):1005-1010.
Dhib-Jalbut SS, Zhan M, Johnson KP, Martin R. Glatiramer acetate reactive blood mononuclear cells respond to myelin antigens with a Th-2 biased phenotype. J Neuroimmunology 2003; 140 :163-171.
Farina et al., "Treatment of multiple sclerosis with Copaxone (COP): Elispot assay detects COP-induced interleukin-4 and interferon-gamma response in blood cells." Brain. Apr. 2001;124(Pt 4):705-19.
Farina et al., "Immunological assay for assessing the efficacy of glatiramer acetate (Copaxone) in multiple sclerosis. A pilot study." J Neurol. Nov. 2002;249(11):1587-92.
Fridkis-Hareli, et al. "Direct binding of myelin basic protein and synthetic copolymer 1 to class II major histocompatibility complex molecules on living antigen-presenting cells-specificity and promiscuity," Proc. Natl. Acad. Sci. USA. 91: 4872-6 (1994).
Fridkis-Hareli, et al., "Binding Motifs of Copolymer 1 to Multiple Sclerosis- and Rheumatoid Arthritis-Associated HLA-DR Molecules" J. Immunol., 1999, 162: 4697-4704.
Fridkis-Hareli et al., "Binding of random copolymers of three amino acids to class II MCH molecules," Intl. Immunol., 1999, 11(5): 635-641.
Fridkis-Hareli et al., "Novel synthetic amino acid copolymers that inhibit autoantigen-specific T cell responses and suppress experimental autoimmune encephalomyelitis." J Clin Invest 109: 1635-1643 (2002).
Frohman et al., (2003) "The utility of MRI in suspected MS: report of Therapeutics and Technology Assessment Subcommittee of the American Academy of Neurology" Neurology Sep. 9, 61(5):602-11.
Gielen et al. "Increased brain-derived neurotrophic factor in white blood cells or RR MS patients" Scand J Immunol 2003, 57:493-97.
Gravel et al., "Adenoviral gene transfer of ciliary neurotrophic factor and brain-derived neurotrophic factor leads to long-term survival of axotomized motor neurons" Nat Med 1997; Jul. 3(7): 765-770.
Grossman et al., "Pharmacogenetics of glatiramer acetate therapy for multiple sclerosis reveals drug-response markers" Pharmacogenetics and Genomics, 2007, 17: 657-666.
Groux et al., "Interleukin-10 induces a long-term antigen specific anergic state in human CD4+ T cells." J. exp. Med. 184 (1996):19-29.
Hirschorn et al., "A comprehensive review of genetic association studies" Genetics in Medicine, Mar. 2002, 4(2): 45-61.
Hong et al. Induction of CD4+CD25+ regulatory T cells by copolymer-I through activation of transcription factor Foxp3. Proc Natl Acad Sci May 3, 2005;102(18):6449-54. Epub Apr. 25, 2005.
Hussein et al. "Glatiramer acetate and IFN-beta act on dendritic cells in multiple sclerosis." J Neuro Immunol (2001)121:102-110.
Imitola et al., "Cytokines in multiple sclerosis: from bench to bedside" PharmacoIoannidis, et al. "Replication validity of genetic association studies" Nature Genetics, Nov. 2001, 29: 306-3091. Ther. 106 (2005) :163-177.
Ioannidis, et al. "Replication validity of genetic association studies" Nature Genetics, Nov. 2001, 29: 306-309.
Jee et al., "CD4(+)CD25(+) regulatory T cells contribute to the therapeutic effects of glatiramer acetate in experimental autoimmune encephalomyelitis." Clin Immunol Oct. 2007;125 (1) :34-42. Epub Jul. 16, 2007.
Johnson D, Hafler DA, Fallis RJ, Lees MB, Brady RO, Quarles RH, Weiner HL., "Cell-mediated immunity to myelin-associated glycoprotein, proteolipid protein, and myelin basic protein in multiple sclerosis.", J Neuroimmunol. Nov. 1986;13 (1):99-108.
Kim et al. "Type 2 monocytes and microglia differentiation mediated by glatiramer acetate therapy in patients with multiple sclerosis." J Immunol (2004) 172:7144-7153.
Lucentini, "Second RNAi pathway emerges" The Scientist, Aug. 2004, 24: 20.

(56) References Cited

OTHER PUBLICATIONS

Martinelli et al. "Effects of glatiramer acetate on relapse rate and accumulated disability in multiple sclerosis: meta-analysis of three double-blind, randomized, placebo-controlled clinical trials." Mult Scler. Aug. 2003; 9(4):349-55.
Martinez et al., "IL-10 suppressor activity and ex-vivo Tr1 cell function are impaired in multiple sclerosis." Eur J Immunol. Feb. 2008;38(2):576-86.
McDonald et al., "Recommended diagnostic criteria for multiple sclerosis: guidelines from the International Panel on the diagnosis of multiple sclerosis." Ann Neurol. Jul. 2001; 50 (1) :121-7.
Mikol et al., Lancet Neurol. Oct. 2008;7(10):903-14. Epub Sep. 11, 2008.
Noseworthy, et al. (2000) "Multiple sclerosis". N Engl J Med., 343: 938-52.
Physician's Desk Reference, Entry: "Copaxone," 2000, Medical Economics Co. Inc., Montvale, NJ, 3115.
Revel M., "Interferon-β in the treatment of relapsing-remitting multiple sclerosis" Pharmacol. Ther., 100(1):49-62 (2003).
Roncarlo "Type-1 regulatory cells." Immunol. Rev. 182(2001):68-80.
Rott et al., "Interleukin 10 prevents experimental allergic encephalomyelitis in rats." Eur. J. Immunol 24(1994):1434-1440.
Sarchielli et al. "Brain-derived neurotrophic factor in patients with multiple sclerosis". J Neuroimmunol Nov. 2002 132(1-2):180-88.
Sarchielli et al. "Production of brain-derived neurotrophic factor by mononuclear cells of patients with multiple sclerosis treated with glatiramer acetate, interferon-beta la, and high doses of immunoglobulins." Mult Scler Apr. 2007;13(3):313-31. Epub Jan. 29, 2007.
Stern et al., "Amino acid copolymer-specific IL-10 secreting regulatory T-cells that ameliorate autoimmune disease in mice." PNAS 2008, 105(13):5172-5176.
Tselis, et al., (2007) "Glatiramer acetate in the treatment of multiple sclerosis" Neuropsychiatric Dis Treat., 3(2): 259-67.
Valenzuela, et al., "Clinical response to glatiramer acetate correlates with modulation of IFN-gamma and IL-4 expression in multiple sclerosis." Mult Scler., Jul. 2007;13(6):754-62.
Valenzuela "Predictive biomarkers of clinical response to Glatiramer Acetate (GA) therapy in Multiple Sclerosis" Presented at: 61st Annual Meeting of the American Academy of Neurology: Apr. 30, 2009, poster.
Valenzuela "Predictive biomarkers of clinical response to Glatiramer Acetate (GA) therapy in Multiple Sclerosis" 2009, poster.
Vieira et al. "Glatiramer acetate (copolymer-1, copaxone) promotes Th2 cell development and increased IL-10 production through modulation of dendritic cells." J Immunol (2003) 170:4483-4488.
Weber et al. "Type II monocytes modulate T cell-mediated central nervous sytem autoimmune disease." Nat Med (2007) 13:935-943.
Wolinsky, et al. (2007) "Glatiramer acetate in primary progressive multiple sclerosis: Results of a multinational, multicenter, double-blind, placebo-controlled trial". Ann Neurol. 61: 14-24.
Copaxone (glatiramer acetate injection), prescribing information, [Feb. 27, 2009] http://www.copaxone.com/pdf/prescribingInformation.pdf.
Clinical Trial Protocol No. 9001, Teva Pharmaceutical Industries, Ltd., first patient enrolled Oct. 23, 1991.
Clinical Trial Protocol No. 9002, Lemmon Co. and Teva Pharmaceutical Industries, Ltd., first patient enrolled Jun. 17, 1993.
Become Trial, Presented at the 23rd Congress of the European Committee for Treatment and Research in Multiple Sclerosis (ECTRIMS) in Prague, Czech Republic. (Oct. 11-14, 2007).
Bjartmaer et al. (2002) "Pathological mechanism and disease progression of multiple sclerosis: therapeutic implications" Drugs of Today 38(1) :17-29.
Comi G, Filippi M. Presented at: 60th Annual Meeting of the American Academy of Neurology: Apr. 12-19, 2008; Chicago, IL. Abstract LBS.003.
Felderhoff-Mueser U. et al. (2005) "IL-18: A key playerin neuroinflammation and neurodegeneration" Trends in Neuroscience 28(9): 487-93.
Guideline of Clinical investigation of medicinal products for the treatment of multiple sclerosis EMEA, London Nov. 16, 2006.
Johnson et al. (1998) "Extended Use of glatiramer acetate (Copaxone) is well tolerated and maintains its clinical effect on multiple sclerosis . . . " Neurology 50:701-708.
Neurostatus, Slightly modified from J.F. Kurtzke, Neurology 1983:33, 1444-52, Ludwig Kappos, MD, Neurology, University Hospital 4031 Basel, Switzerland.
Wolinsky J.S. (2006) "The use of glatiramer acetate in the treatment of multiple sclerosis" Advances in Neurology 98:273-292.
Zwibel et al., Glatiramer acetate in treatment-naïve and prior interferon-β-1b-treated multiple sclerosis patients, Acta Neurologica Scanoinavica, 2006, 113: 378-386.
Patent Examination Report No. 2 issued by the Australian Government IP Australia on Oct. 28, 2016 in connection with Australian Patent Application No. 2011313842.
Patent Examination Report No. 1 issued by the Australian Government IP Australia on Nov. 27, 2015 in connection with Australian Patent Application No. 2011313842.
English translation of the First Office Action issued by the Japanese Patent Office on Sep. 6, 2016 in connection with Japanese Patent Application No. 2013-533913 (Japanese Appeal No. 2016-6677).
English translation of the Pre-appeal Examination Report drafted by the Japanese Patent Office on Jul. 20, 2016 in connection with Japanese Patent Application No. 2013-533913 (Japanese Appeal No. 2016-006677).
English translation of the First Office Action issued by the Mexican Patent Office on Jul. 6, 2016 in connection with Mexican Patent Application No. MX/a/2013/003929.
English translation of the Second Office Action issued by the Mexican Patent Office on Oct. 10, 2016 in connection with Mexican Patent Application No. MX/a/2013/003929.

\* cited by examiner

Figure 1A

Time Line Showing Responders' EDSS Score with GA Treatment

Cytokine Levels Secreted by the PBMCs of Responders at
Baseline and After 2 Months of GA Treatment.

Figure 2B

Cytokine Levels Secreted by the PBMCs of Non-Responders at Baseline and After 2 Months of GA Treatment.

CYTOKINE BIOMARKERS AS PREDICTIVE BIOMARKERS OF CLINICAL RESPONSE FOR GLATIRAMER ACETATE

This application is a divisional of U.S. Ser. No. 14/250,955, filed Apr. 11, 2014, now allowed, which is a divisional of U.S. Ser. No. 13/269,913, filed Oct. 10, 2011, now U.S. Pat. No. 8,709,433, which claims the benefit of U.S. Provisional Application No. 61/391,968, filed Oct. 11, 2010, the contents of each of which are hereby incorporated by reference in their entirety into this application.

Throughout this application various publications are referenced by their full citations in parentheses. The disclosures of these publications in their entireties are hereby incorporated by reference into this application in order to more fully describe the state of the art to which this invention pertains.

BACKGROUND OF THE INVENTION

Multiple sclerosis (MS) is a chronic, debilitating autoimmune disease of the central nervous system (CNS) with either relapsing-remitting (RR) or progressive course leading to neurologic deterioration and disability. At time of initial diagnosis, RRMS is the most common form of the disease (1) which is characterized by unpredictable acute episodes of neurological dysfunction (relapses), followed by variable recovery and periods of clinical stability. The vast majority of RRMS patients eventually develop secondary progressive (SP) disease with or without superimposed relapses. Around 15% of patients develop a sustained deterioration of their neurological function from the beginning; this form is called primary progressive (PP) MS. Patients who have experienced a single clinical event (Clinically Isolated Syndrome or "CIS") and who show lesion dissemination on subsequent magnetic resonance imaging (MRI) scans according to McDonald's criteria, are also considered as having relapsing MS.(2)

With a prevalence that varies considerably around the world, MS is the most common cause of chronic neurological disability in young adults.(3,4) Anderson et al. estimated that there were about 350,000 physician-diagnosed patients with MS in the United States in 1990 (approx. 140 per 100,000 population).(5) It is estimated that about 2.5 million individuals are affected worldwide.(6) In general, there has been a trend toward an increasing prevalence and incidence of MS worldwide, but the reasons for this trend are not fully understood.(5)

Current therapeutic approaches consist of i) symptomatic treatment ii) treatment of acute relapses with corticosteroids and iii) treatment aimed to modify the course of the disease. Currently approved therapies target the inflammatory processes of the disease. Most of them are considered to act as immunomodulators but their mechanisms of action have not been completely elucidated. Immunosuppressants or cytotoxic agents are also used in some patients after failure of conventional therapies. Several medications have been approved and clinically ascertained as efficacious for the treatment of RR-MS; including BETASERON®, AVONEX® and REBIF®, which are derivatives of the cytokine interferon beta (IFNB), whose mechanism of action in MS is generally attributed to its immunomodulatory effects, antagonizing pro-inflammatory reactions and inducing suppressor cells.(7) Other approved drugs for the treatment of MS include Mitoxantrone and Natalizumab.

Glatiramer Acetate

Glatiramer acetate (GA) is the active substance in Copaxone®, a marketed product indicated for reduction of the frequency of relapses in patients with RRMS. Its effectiveness in reducing relapse rate and disability accumulation in RR-MS is comparable to that of other available immunomodulating treatments.(8,9,10) Glatiramer acetate consists of the acetate salts of synthetic polypeptides containing four naturally occurring amino acids: L-glutamic acid, L-alanine, L-tyrosine and L-lysine. The average molecular weight of glatiramer acetate is between 5,000 and 9,000 Daltons. At a daily standard dose of 20 mg, GA is generally well tolerated, however response to the drug is variable. In various clinical trials, GA reduced relapse rates and progression of disability in patients with RR-MS. The therapeutic effect of GA is supported by the results of magnetic resonance imaging (MRI) findings from various clinical centers (11), however there are no validated predictive biomarkers of response to GA treatment.

A possible initial mode of action of GA is associated with binding to MHC molecules and consequent competition with various myelin antigens for their presentation to T cells.(12) A further aspect of its mode of action is the potent induction of T helper 2 (Th2) type cells that presumably can migrate to the brain and lead to in situ bystander suppression.(13) It has been shown that GA treatment in MS results in the induction of GA-specific T cells with predominant Th2 phenotype both in response to GA and cross-reactive myelin antigens.(13,14) Furthermore, the ability of GA-specific infiltrating cells to express anti-inflammatory cytokines such as IL-10 and transforming growth factor-beta (TGF-β) together with brain-derived neurotrophic factor (BDNF) seem to correlate with the therapeutic activity of GA in EAE.(15,16,17)

Clinical experience with GA consists of information obtained from completed and ongoing clinical trials and from post-marketing experience. The clinical program includes three double-blind, placebo-controlled studies in RRMS subjects treated with GA 20 mg/day.(18,19,20) A significant reduction in the number of relapses, compared with placebo, was seen. In the largest controlled study, the relapse rate was reduced by 32% from 1.98 under placebo to 1.34 under GA 20 mg. GA 20 mg has also demonstrated beneficial effects over placebo on MRI parameters relevant to RRMS. A significant effect in median cumulative number of Gd-enhancing lesions over 9 months of treatment (11 lesions in the 20 mg group compared to 17 lesions under placebo) was demonstrated.

The clinical program with GA also includes one double-blind study in chronic-progressive MS subjects,(21) one double-blind placebo-controlled study in primary progressive patients,(22) one double-blind placebo-controlled study in CIS patients(23) and numerous open-label and compassionate use studies, mostly in RRMS. The clinical use of GA has been extensively reviewed and published in the current literature (24,25,26,27).

An important tool for the therapeutic management of those with relapsing MS is the ability to determine the likelihood of treatment success. The identification of those individuals that will respond to GA has been elusive. As the therapeutic options for MS increase, the importance of being able to determine who will respond favorably to therapy and specifically to GA, has become of increasing significance.

SUMMARY OF THE INVENTION

This invention provides a method for treating a human subject afflicted with multiple sclerosis or a single clinical attack consistent with multiple sclerosis with a pharmaceutical composition comprising glatiramer acetate and a pharmaceutically acceptable carrier, comprising the steps of determining whether the human subject is a glatiramer acetate responder by evaluating a biomarker selected from the group consisting of IL-17 concentration, TNF-α concentration, IL-2 concentration and IFN-γ concentration, or a combination thereof, in the blood of the human subject and administering the pharmaceutical composition comprising glatiramer acetate and a pharmaceutically acceptable carrier to the human subject only if the human subject is identified as a glatiramer acetate responder.

This invention also provides a method of predicting clinical responsiveness to glatiramer acetate therapy in a human subject afflicted with multiple sclerosis or a single clinical attack consistent with multiple sclerosis, the method comprising evaluating a biomarker selected from the group consisting of IL-concentration, TNF-α concentration, IL-2 concentration and IFN-γ concentration, or a combination thereof, in the blood of the human subject, to thereby predict clinical responsiveness to glatiramer acetate.

This invention also provides a method for treating a human subject afflicted with multiple sclerosis or a single clinical attack consistent with multiple sclerosis comprising the steps of administering to the human subject a therapeutic amount of a pharmaceutical composition comprising glatiramer acetate and a pharmaceutically acceptable carrier, determining whether the human subject is a glatiramer acetate responder by evaluating a biomarker selected from the group consisting of IL-17 concentration, INF-α concentration, IL-2 concentration and IFN-γ concentration, or a combination thereof, in the blood of the human subject, and continuing administration of the pharmaceutical composition if the human subject is identified as a glatiramer acetate responder, or modifying the administration of the pharmaceutical composition to the human subject if the human subject is not identified as a glatiramer acetate responder.

DETAILED DESCRIPTION OF THE INVENTION

This invention provides a method for treating a human subject afflicted with multiple sclerosis or a single clinical attack consistent with multiple sclerosis with a pharmaceutical composition comprising glatiramer acetate and a pharmaceutically acceptable carrier, comprising the steps of determining whether the human subject is a glatiramer acetate responder by evaluating a biomarker selected from the group consisting of IL-17 concentration, TNF-α concentration, IL-2 concentration and IFN-γ concentration, or a combination thereof, in the blood of the human subject and administering the pharmaceutical composition comprising glatiramer acetate and a pharmaceutically acceptable carrier to the human subject only if the human subject is identified as a glatiramer acetate responder.

In an embodiment, administering the pharmaceutical composition comprising glatiramer acetate and a pharmaceutically acceptable carrier comprises administering to the human subject three subcutaneous injections of the pharmaceutical composition over a period of seven days with at least one day between every subcutaneous injection.

In an embodiment, the pharmaceutical composition is a unit dose of a 0.5 ml aqueous solution comprising 20 mg of glatiramer acetate.

In an embodiment, the IL-17 concentration, TNF-α concentration, IL-2 concentration and IFN-γ concentration, or the combination thereof is a PBMC supernatant concentration.

In an embodiment, the IL-17 concentration, TNF-α concentration, IL-2 concentration and IFN-γ concentration, or the combination thereof is observed at pretreatment.

In an embodiment, the IL-17 concentration, INF-α concentration, IL-2 concentration and INF-γ concentration, or the combination thereof is observed at 2 months after the first administration of glatiramer acetate.

In an embodiment, if the human subject is identified as a glatiramer acetate responder, the human subject is thereafter administered the pharmaceutical composition comprising glatiramer acetate and a pharmaceutically acceptable carrier as monotherapy.

In an embodiment, if the human subject is identified as a glatiramer acetate responder, the human subject is thereafter administered a pharmaceutical composition comprising glatiramer acetate and a pharmaceutically acceptable carrier, and the human subject is also thereafter administered another multiple sclerosis drug which is not glatiramer acetate. In a further embodiment, the multiple sclerosis drug is selected from Interferon, Mitoxantrone and Natalizumab.

In an embodiment, if the human subject is not identified as a glatiramer acetate responder, the human subject is thereafter administered a multiple sclerosis drug which is not glatiramer acetate.

In an embodiment, if the human subject is not identified as a glatiramer acetate responder, the human subject is thereafter administered a multiple sclerosis drug which is not glatiramer acetate, and the human subject is not thereafter administered glatiramer acetate.

In an embodiment, the multiple sclerosis drug is selected from Interferon, Mitoxantrone and Natalizumab.

In an embodiment, the biomarker is IL-17 concentration.

In an embodiment, the biomarker is IL-17(A) concentration. In a further embodiment, an IL-17 concentration or an IL-17(A) concentration greater than or equal to 120 pg/ml is associated with a human subject identified as a glatiramer acetate responder.

In an embodiment, the biomarker is TNF-α concentration. In a further embodiment, a TNF-α concentration greater than or equal to 20000 pg/ml is associated with a human subject identified as a glatiramer acetate responder.

In an embodiment, the biomarker is IFN-γ concentration. In a further embodiment, an IFN-γ concentration greater than or equal to 6000 pg/ml is associated with a human subject identified as a glatiramer acetate responder.

In an embodiment, the biomarker is IL-2 concentration. In a further embodiment, an IL-2 concentration greater than or equal to 30000 pg/ml is associated with a human subject identified as a glatiramer acetate responder.

In an embodiment, the human subject is a naive patient.

In an embodiment, the human subject has been previously administered a multiple sclerosis drug other than glatiramer acetate. In a further embodiment, the previously administered multiple sclerosis drug is selected from Interferon, Mitoxantrone and Natalizumab.

This invention also provides a method of predicting clinical responsiveness to glatiramer acetate therapy in a human subject afflicted with multiple sclerosis or a single clinical attack consistent with multiple sclerosis, the method comprising evaluating a biomarker selected from the group consisting of IL-concentration, INF-α concentration, IL-2 concentration and IFN-γ concentration, or a combination thereof, in the blood of the human subject, to thereby predict clinical responsiveness to glatiramer acetate.

In an embodiment, the glatiramer acetate therapy comprises administering to the human subject three subcutaneous injections of a pharmaceutical composition comprising glatiramer acetate and a pharmaceutically acceptable carrier over a period of seven days with at least one day between every subcutaneous injection. In a further embodiment, the pharmaceutical composition is a unit dose of a 0.5 ml aqueous solution comprising 20 mg of glatiramer acetate.

In an embodiment, the IL-17 concentration, INF-α concentration, IL-2 concentration and IFN-γ concentration, or the combination thereof is a PBMC supernatant concentration.

In an embodiment, the IL-17 concentration, INF-α concentration, IL-2 concentration and IFN-γ concentration, or the combination thereof is observed at pretreatment.

In an embodiment, the IL-17 concentration, INF-α concentration, IL-2 concentration and INF-γ concentration, or the combination thereof is observed at 2 months after the first administration of glatiramer acetate.

In an embodiment, if the human subject is identified as a glatiramer acetate responder, the human subject is thereafter administered the pharmaceutical composition comprising glatiramer acetate and a pharmaceutically acceptable carrier as monotherapy.

In an embodiment, if the human subject is identified as a glatiramer acetate responder, the human subject is thereafter administered a pharmaceutical composition comprising glatiramer acetate and a pharmaceutically acceptable carrier, and the human subject is also thereafter administered another multiple sclerosis drug which is not glatiramer acetate. In a further embodiment, the multiple sclerosis drug is selected from Interferon, Mitoxantrone and Natalizumab.

In an embodiment, if the human subject is not identified as a glatiramer acetate responder, the human subject is thereafter administered a multiple sclerosis drug which is not glatiramer acetate.

In an embodiment, if the human subject is not identified as a glatiramer acetate responder, the human subject is thereafter administered a multiple sclerosis drug which is not glatiramer acetate, and the human subject is not thereafter administered glatiramer acetate.

In an embodiment, the multiple sclerosis drug is selected from Interferon, Mitoxantrone and Natalizumab.

In an embodiment, the biomarker is IL-17 concentration.

In an embodiment, the biomarker is IL-17(A) concentration. In a further embodiment, an IL-17 concentration or an IL-17(A) concentration greater than or equal to 120 pg/ml is associated with a human subject identified as a glatiramer acetate responder.

In an embodiment, the biomarker is TNF-α concentration. In a further embodiment, a TNF-α concentration greater than or equal to 20000 pg/ml is associated with a human subject identified as a glatiramer acetate responder.

In an embodiment, the biomarker is IFN-γ concentration. In a further embodiment, an IFN-γ concentration greater than or equal to 6000 pg/ml is associated with a human subject identified as a glatiramer acetate responder.

In an embodiment, the biomarker is IL-2 concentration. In a further embodiment, an IL-2 concentration greater than or equal to 30000 pg/ml is associated with a human subject identified as a glatiramer acetate responder.

In an embodiment, the human subject is a naive patient.

In an embodiment, the human subject has been previously administered a multiple sclerosis drug other than glatiramer acetate. In a further embodiment, the previously administered multiple sclerosis drug is selected from Interferon, Mitoxantrone and Natalizumab.

This invention also provides a method for treating a human subject afflicted with multiple sclerosis or a single clinical attack consistent with multiple sclerosis comprising the steps of administering to the human subject a therapeutic amount of a pharmaceutical composition comprising glatiramer acetate and a pharmaceutically acceptable carrier, determining whether the human subject is a glatiramer acetate responder by evaluating a biomarker selected from the group consisting of IL-17 concentration, TNF-α concentration, IL-2 concentration and IFN-γ concentration, or a combination thereof, in the blood of the human subject, and continuing administration of the pharmaceutical composition if the human subject is identified as a glatiramer acetate responder, or modifying the administration of the pharmaceutical composition to the human subject if the human subject is not identified as a glatiramer acetate responder.

In an embodiment, administering to the human subject a therapeutic amount of a pharmaceutical composition comprising glatiramer acetate and a pharmaceutically acceptable carrier comprises administering to the human subject three subcutaneous injections of the pharmaceutical composition over a period of seven days with at least one day between every subcutaneous injection.

In an embodiment, the pharmaceutical composition is a unit dose of a 0.5 ml aqeuous solution comprising 20 mg of glatiramer acetate.

In an embodiment, the IL-17 concentration, INF-α concentration, IL-2 concentration and IFN-γ concentration, or the combination thereof is a PBMC supernatant concentration.

In an embodiment, the IL-17 concentration, INF-α concentration, IL-2 concentration and IFN-γ concentration, or the combination thereof is observed at pretreatment.

In an embodiment, the IL-17 concentration, INF-α concentration, IL-2 concentration and INF-γ concentration, or the combination thereof is observed at 2 months after the first administration of glatiramer acetate.

In an embodiment, if the human subject is identified as a glatiramer acetate responder, the human subject is thereafter administered the pharmaceutical composition comprising glatiramer acetate and a pharmaceutically acceptable carrier as monotherapy.

In an embodiment, if the human subject is identified as a glatiramer acetate responder, the human subject is thereafter administered a pharmaceutical composition comprising glatiramer acetate and a pharmaceutically acceptable carrier, and the human subject is also thereafter administered another multiple sclerosis drug which is not glatiramer acetate. In a further embodiment, the multiple sclerosis drug is selected from Interferon, Mitoxantrone and Natalizumab.

In an embodiment, if the human subject is not identified as a glatiramer acetate responder, the human subject is thereafter administered a multiple sclerosis drug which is not glatiramer acetate.

In an embodiment, if the human subject is not identified as a glatiramer acetate responder, the human subject is thereafter administered a multiple sclerosis drug which is not glatiramer acetate, and the human subject is not thereafter administered glatiramer acetate.

In an embodiment, the multiple sclerosis drug is selected from Interferon, Mitoxantrone and Natalizumab.

In an embodiment, the biomarker is IL-17 concentration.

In an embodiment, the biomarker is IL-17(A) concentration. In a further embodiment, an IL-17 concentration or an IL-17(A) concentration greater than or equal to 120 pg/ml is associated with a human subject identified as a glatiramer acetate responder.

In an embodiment, the biomarker is TNF-α concentration. In a further embodiment, a TNF-α concentration greater than or equal to 20000 pg/ml is associated with a human subject identified as a glatiramer acetate responder.

In an embodiment, the biomarker is IFN-γ concentration. In a further embodiment, an IFN-γ concentration greater than or equal to 6000 pg/ml is associated with a human subject identified as a glatiramer acetate responder.

In an embodiment, the biomarker is IL-2 concentration. In a further embodiment, an IL-2 concentration greater than or equal to 30000 pg/ml is associated with a human subject identified as a glatiramer acetate responder.

In an embodiment, the human subject is a naive patient.

In an embodiment, the human subject has been previously administered a multiple sclerosis drug other than glatiramer acetate. In a further embodiment, the previously administered multiple sclerosis drug is selected from Interferon, Mitoxantrone and Natalizumab.

DEFINITIONS

Forms of Multiple Sclerosis:
There are five distinct disease stages and/or types of MS:
1) benign multiple sclerosis;
2) relapsing-remitting multiple sclerosis (RRMS);
3) secondary progressive multiple sclerosis (SPMS);
4) progressive relapsing multiple sclerosis (PRMS); and
5) primary progressive multiple sclerosis (PPMS).

Benign multiple sclerosis is a retrospective diagnosis which is characterized by 1-2 exacerbations with complete recovery, no lasting disability and no disease progression for 10-15 years after the initial onset. Benign multiple sclerosis may, however, progress into other forms of multiple sclerosis.

Patients suffering from RRMS experience sporadic exacerbations or relapses, as well as periods of remission. Lesions and evidence of axonal loss may or may not be visible on MRI for patients with RRMS.

SPMS may evolve from RRMS. Patients afflicted with SPMS have relapses, a diminishing degree of recovery during remissions, less frequent remissions and more pronounced neurological deficits than RRMS patients. Enlarged ventricles, which are markers for atrophy of the corpus callosum, midline center and spinal cord, are visible on MRI of patients with SPMS.

PPMS is characterized by a steady progression of increasing neurological deficits without distinct attacks or remissions. Cerebral lesions, diffuse spinal cord damage and evidence of axonal loss are evident on the MRI of patients with PPMS. PPMS has periods of acute exacerbations while proceeding along a course of increasing neurological deficits without remissions. Lesions are evident on MRI of patients suffering from PRMS.(28)

A clinically isolated syndrome (CIS) is a single monosymptomatic attack compatible with MS, such as optic neuritis, brain stem symptoms, and partial myelitis. Patients with CIS that experience a second clinical attack are generally considered to have clinically definite multiple sclerosis (CDMS). Over 80 percent of patients with a CIS and MRI lesions go on to develop MS, while approximately 20 percent have a self-limited process.(29,30) Patients who experience a single clinical attack consistent with MS may have at least one lesion consistent with multiple sclerosis prior to the development of clinically definite multiple sclerosis.

Multiple sclerosis may present with optic neuritis, blurring of vision, diplopia, involuntary rapid eye movement, blindness, loss of balance, tremors, ataxia, vertigo, clumsiness of a limb, lack of co-ordination, weakness of one or more extremity, altered muscle tone, muscle stiffness, spasms, tingling, paraesthesia, burning sensations, muscle pains, facial pain, trigeminal neuralgia, stabbing sharp pains, burning tingling pain, slowing of speech, slurring of words, changes in rhythm of speech, dysphagia, fatigue, bladder problems (including urgency, frequency, incomplete emptying and incontinence), bowel problems (including constipation and loss of bowel control), impotence, diminished sexual arousal, loss of sensation, sensitivity to heat, loss of short term memory, loss of concentration, or loss of judgment or reasoning.

Relapsing Form of Multiple Sclerosis:
The term relapsing MS includes:
1) patients with RRMS;
2) patients with SPMS and superimposed relapses; and
3) patients with CIS who show lesion dissemination on subsequent MRI scans according to McDonald's criteria.

As used herein, relapsing forms of multiple sclerosis include: Relapsing-remitting multiple sclerosis (RRMS), characterized by unpredictable acute episodes of neurological dysfunction (relapses), followed by variable recovery and periods of clinical stability;

Secondary Progressive MS (SPMS), wherein patients having RRMS develop sustained deterioration with or without relapses superimposed; and Primary progressive-relapsing multiple sclerosis (PPRMS) or progressive-relapsing multiple sclerosis (PRMS), an uncommon form wherein patients developing a progressive deterioration from the beginning can also develop relapses later on.

Kurtzke Expanded Disability Status Scale (EDSS):
The Kurtzke Expanded Disability Status Scale (EDSS) is a method of quantifying disability in multiple sclerosis. The EDSS replaced the previous Disability Status Scales which used to bunch people with MS in the lower brackets. The EDSS quantifies disability in eight Functional Systems (FS) and allows neurologists to assign a Functional System Score (FSS) in each of these. The Functional Systems are: pyramidal, cerebellar, brainstem, sensory, bowel and bladder, visual & cerebral (according to www.mult-sclerosis.org/expandeddisabilitystatusscale).

Clinical Relapse:
A clinical relapse, which may also be used herein as "relapse," "confirmed relapse," or "clinically defined relapse," is defined as the appearance of one or more new neurological abnormalities or the reappearance of one or more previously observed neurological abnormalities.

This change in clinical state must last at least 48 hours and be immediately preceded by a relatively stable or improving neurological state of at least 30 days. This criterion is different from the clinical definition of exacerbation "at least 24 hours duration of symptoms," (31) as detailed in the section "relapse evaluation."

An event is counted as a relapse only when the subject's symptoms are accompanied by observed objective neurological changes, consistent with:
  a) an increase of at least 1.00 in the EDSS score or one grade in the score of two or more of the seven FS (32); or,
  b) two grades in the score of one of FS as compared to the previous evaluation.

The subject must not be undergoing any acute metabolic changes such as fever or other medical abnormality. A change in bowel/bladder function or in cognitive function must not be entirely responsible for the changes in EDSS or FS scores.

As used herein, "in the blood of the subject" is represented by "serum" and also the "supernatant" of PBMCs derived from the subject's blood.

As used herein, the "supernatant" refers to supernatants collected from Peripheral blood mononuclear cells (PBMCs) purified from subject blood samples, and stimulated as described in the methods hereinbelow. The stimulation may be performed in either freshly isolated PBMCs or in cryopreserved cells after thawing.

As used herein, "concentration observed at" a certain time-point refers to a concentration measured in the supernatant of PBMC derived from the subject's blood at that certain time point. The concentration may be measured in freshly isolated cells or in cryopreserved cells after thawing.

As used herein, "pretreatment" refers to any time point after diagnosis with MS or CIS and before beginning of treatment with a composition comprising GA.

As used herein, a "multiple sclerosis drug" is a drug or an agent intended to treat clinically defined MS, CIS, any form of neurodegenerative or demyelinating diseases, or symptoms of any of the above mentioned diseases. "Multiple sclerosis drugs" may include but are not limited to antibodies, immunosuppressants, anti-inflammatory agents, immunomodulators, cytokines, cytotoxic agents and steroids and may include approved drugs, drugs in clinical trial, or alternative treatments, intended to treat clinically defined MS, CIS or any form of neurodegenerative or demyelinating diseases. "Multiple sclerosis drugs" include but are not limited to Interferon and its derivatives (including BETASERON®, AVONEX® and REBIF®), Mitoxantrone and Natalizumab. Agents approved or in-trial for the treatment of other autoimmune diseases, but used in a MS or CIS patient to treat MS or CIS are also defined as multiple sclerosis drugs.

As used herein, a "naive patient" is a subject that has not been treated with any multiple sclerosis drugs as defined in the former paragraph.

Experimental Details

Example

Evaluating Cytokine Levels in Patients Classified as Responders or Non-Responders to GA Methods
Subjects and Cells:
Relapsing-remitting multiple sclerosis patients (n=12) were treated with either 20 mg GA or 40 mg GA daily in the Teva FORTE clinical trial(www.medicalnewstoday.com/articles/48863.php). Whole blood was taken from patients at three time points including baseline (baseline, month 2 and month 6). Peripheral blood mononuclear cells (PBMCs) were cryopreserved at baseline, month 2 and month 6.

The incidence of clinical relapses, and the expanded disability status scale score (EDSS) after 12 months treatment were used to define patients as responders (no clinical relapse during the test period) or non-responders (1 or more clinical relapses as defined hereinbelow). Several patients were withdrawn from drug within the treatment year due to adverse responses and were not included in this analysis.

Figure 2A:
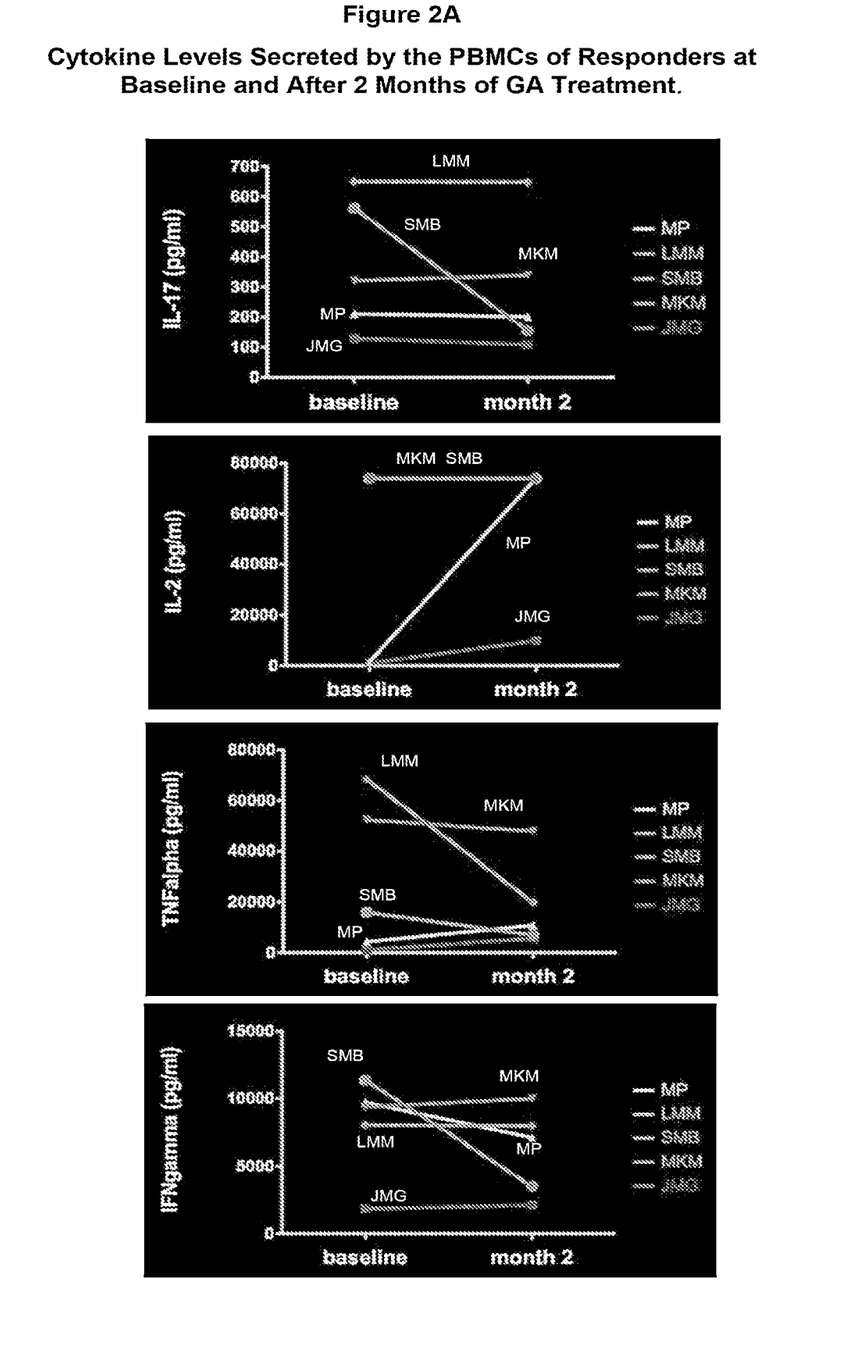
FIG. 2A: Cytokine levels secreted by the Peripheral blood mononuclear cells (PBMCs) of responders at baseline and after 2 months of GA treatment.
Figure 2B:
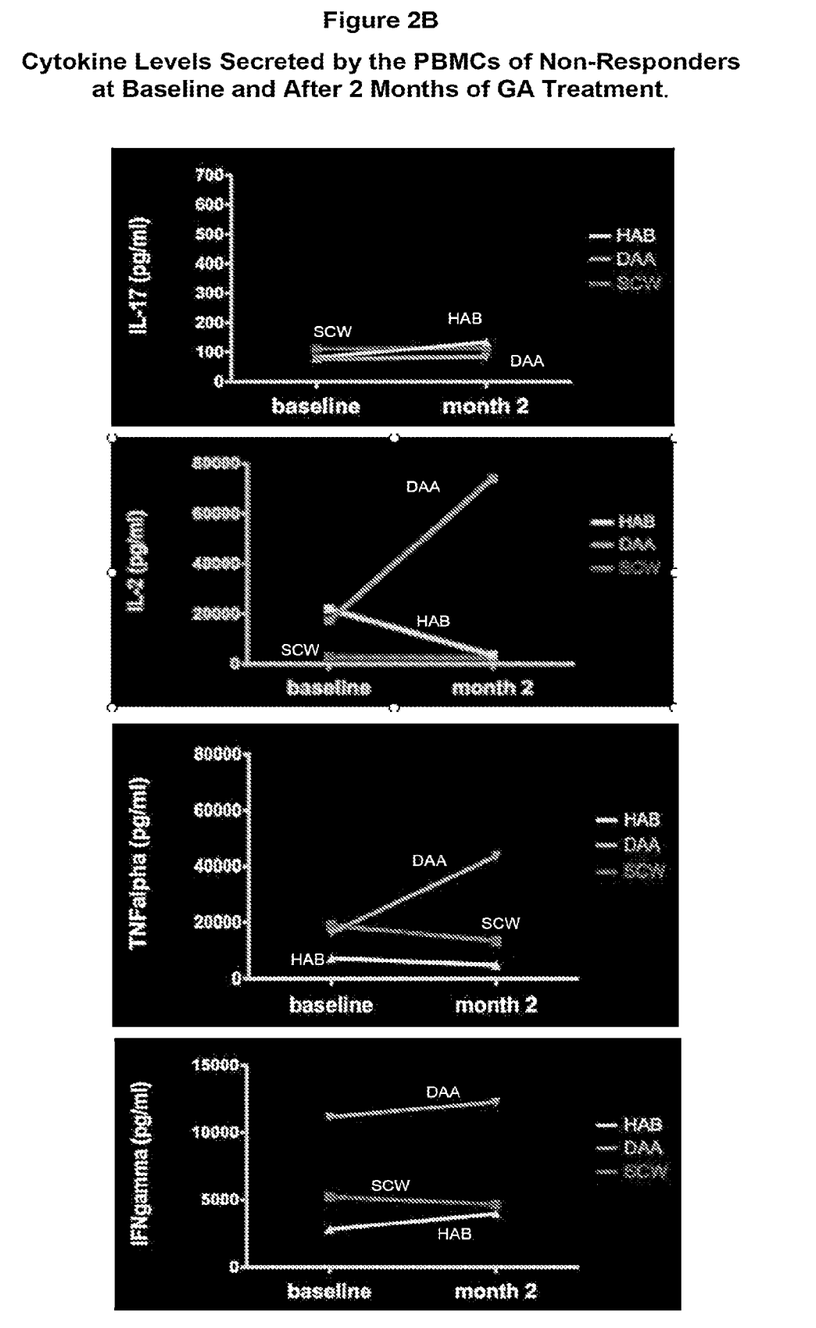
FIG. 2B: Cytokine levels secreted by PBMCs of non-responders at baseline and after 2 months of GA treatment.

Multiplex Cytokine Assay
Blood was drawn from patients at baseline, 2 months and 6 months. Peripheral Blood Mononuclear Cells (PBMCs) were purified from the blood using a Ficoll-Hypaque gradient and cryopreserved. Cryopreserved PBMCs from each time point were thawed, rested overnight in AIM V medium supplemented with 5% human serum, and stimulated with PMA (1 mg/ml; SIGMA) and ionomycin (5 mg/ml; SIGMA) for 6 hours (40,000 PBMCs in 200 microliters final volume). Supernatants were removed from stimulated and unstimulated cells and stored at −20° C. until assay with a human 27-plex kit (Bio-Rad Laboratories, Hercules, Calif.). Data was acquired using a Bio-Plex Array Reader and analyzed with Bio-Plex Manager 4 software (Bio-Rad). Graphs were drawn using Prism software (GraphPad Software, Inc.). We performed both 2-plex (IL-17 and IFNγ) and 27 multiplex (including 27 human cytokines) were used in this comprehensive cytokine analysis. The multiplex data from these two assays were individualized on a per patient basis and presented in FIG. 2.

Relapse Evaluation
A clinical relapse was defined as the appearance of one or more new neurological abnormalities or the reappearance of one or more previously observed neurological abnormalities.

This change in clinical state lasted at least 48 hours and was immediately preceded by a relatively stable or improving neurological state of at least 30 days. The criterion used in the study was different from the clinical definition of exacerbation "at least 24 hours duration of symptoms". (31) Since "in study" exacerbation definition must be supported by an objective neurological evaluation (see next paragraph), a neurological deficit must sustain long enough to eliminate pseudo exacerbations.

An event was counted as a relapse only when the subject's symptoms were accompanied by observed objective neurological changes, consistent with:
  a) an increase of at least 1.00 in the EDSS score or one grade in the score of two or more of the seven FS (32); or,
  b) two grades in the score of one of FS as compared to the previous evaluation.

The subject was not undergoing any acute metabolic changes such as fever or other medical abnormality. A change in bowel/bladder function or in cognitive function was not entirely responsible for the changes in EDSS or FS scores.

Subject Evaluation by the Examining Neurologist
A complete neurological assessment was performed at months −1 (screening), 0 (baseline), 3, 6, 9, 12 (end of double-blind phase), 18 and 24 (termination/early discontinuation).

Relapse Determination by the Treating Neurologist
The decision as to whether the neurological change was considered a confirmed relapse was made by the Treating Physician, based on EDSS/FS actual (not converted) scores assessed by the Examining Neurologist.

Follow-up visits to monitor the course of the relapse were made at the Treating Physician's discretion, in addition to the assessment at the next scheduled visit, but the neurological assessments were performed by the Examining Neurologist.

Relapse Evaluation Procedures

Subjects were instructed to telephone their study site within 48 hours should any symptoms suggestive of a relapse appear.

The Examining Neurologist evaluated the subject within 7 days of symptoms onset, conditional upon a symptomatic period of ≥48 hours. The Treating Neurologist/Physician evaluated the subject once any symptom suggestive of a relapse occurred.

In case of a suggestive relapse during a scheduled or unscheduled visit, the Treating Neurologist/Physician referred the subject to the Examining eurologist/Physician.

Results

These findings demonstrate increased levels of IL-17(A), TNF-alpha, IL-2 and IFN-gamma, at the baseline and 2 months time points, in those individuals who were without clinically defined relapses in the one year trial period post initiation of treatment. To the contrary, we observed substantially lower levels of these same pro-inflammatory cytokines in those who had clinically defined relapses during the trial period (see FIG. 1 and FIG. 2).

Discussion

Figure 1A:
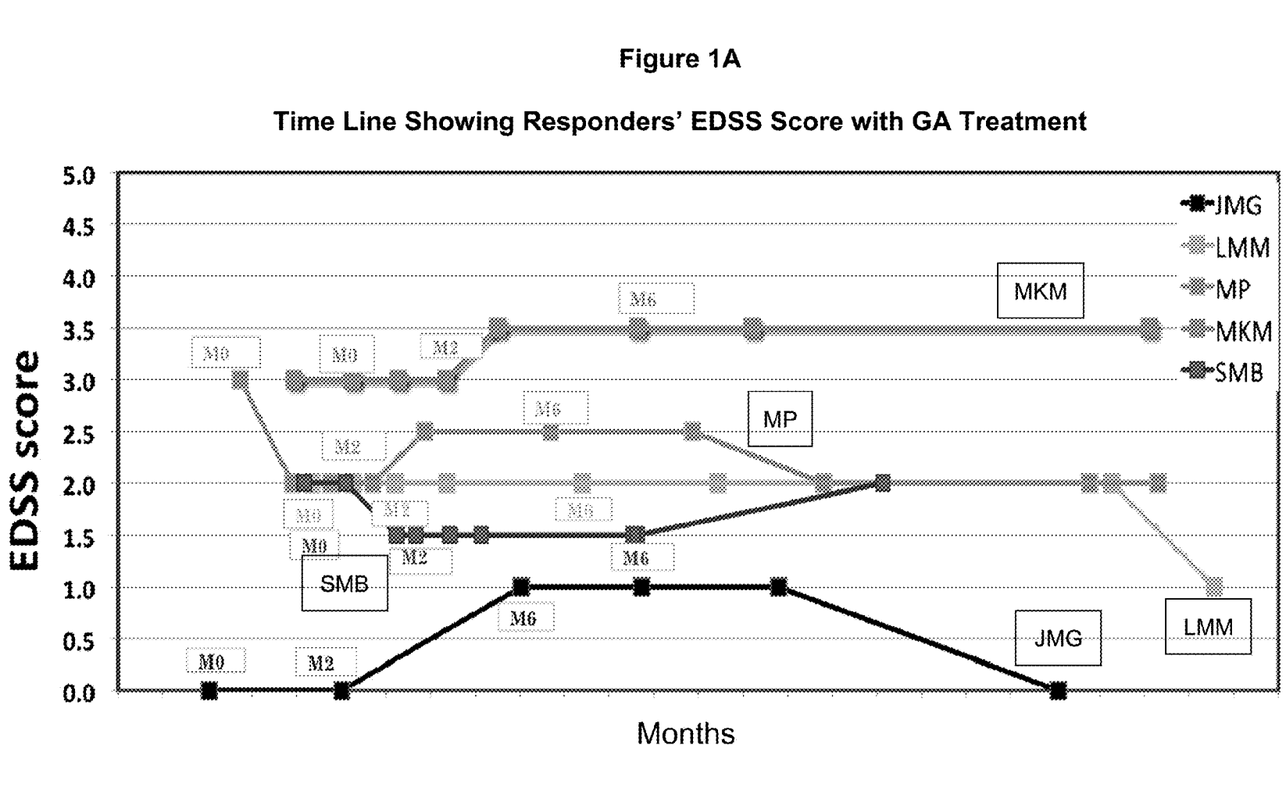
FIG. 1A: Time line showing responders' EDSS score with GA treatment.
Figure 1B:
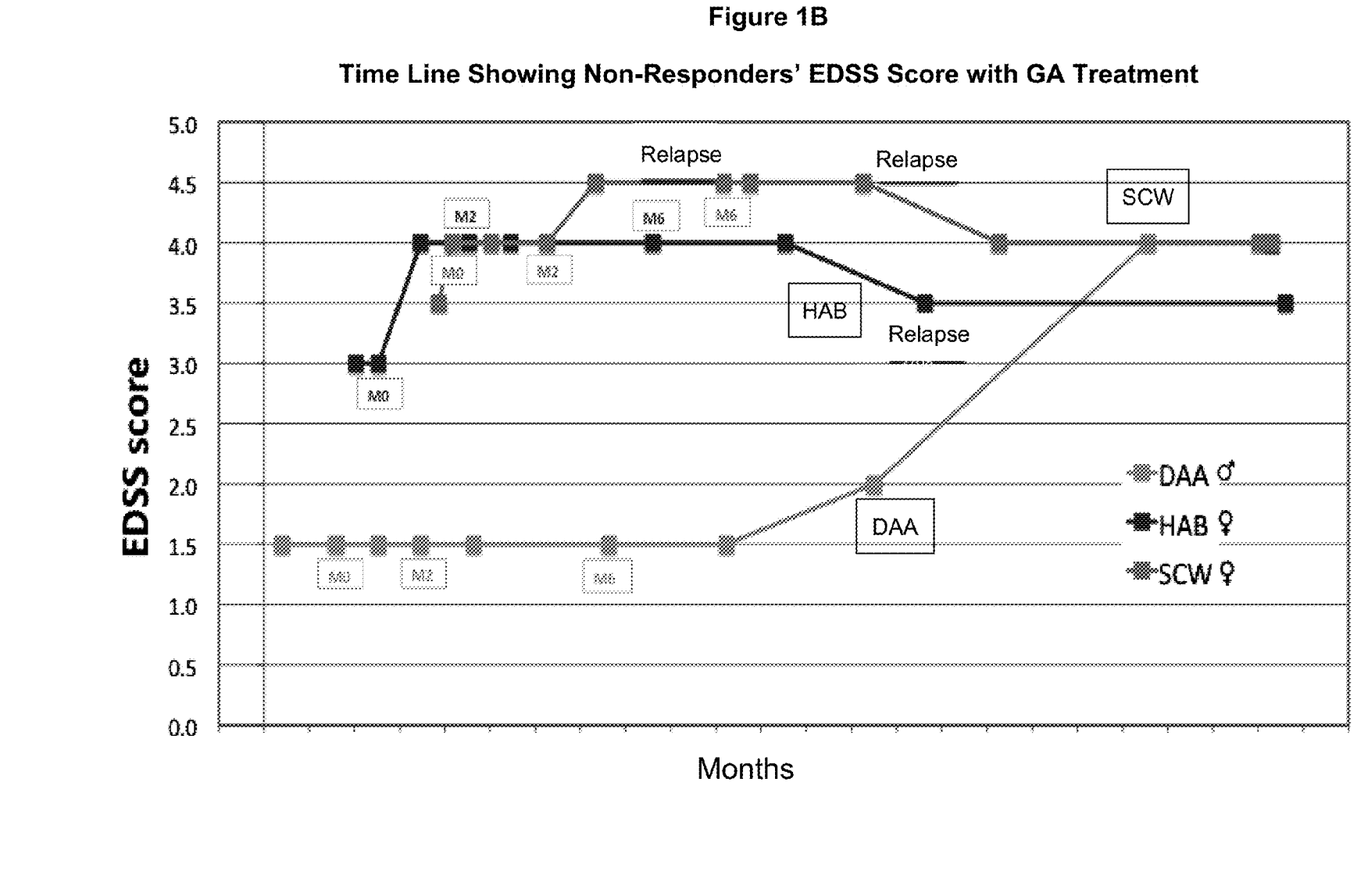
FIG. 1B: Time line showing non-responders' EDSS score with GA treatment.

For this study, PBMC were obtained at baseline, 2 months and 6 months post initiation of treatment with glatiramer acetate. The findings demonstrate increased levels of IL-17 (A), IL-2, TNFα, and IFNγ at baseline and 2 months after the beginning of treatment with GA, in those individuals who were without clinically defined relapses in the one year trial period post initiation of treatment. To the contrary, substantially lower levels of these same pro-inflammatory cytokines were found in those who had clinically defined relapses during the trial period as shown in FIG. 1.

Ex vivo assays have been used to monitor the immunological effects of GA in GA-treated MS patients. For example, Hohlfeld et al. reported: (1) a significant reduction of GA-induced PBMC proliferation; (2) a positive IL-4 ELISPOT response mediated predominantly by CD4 cells after stimulation with GA; and (3) an elevated IFN-gamma response partially mediated by CD8 cells after stimulation with high GA concentrations, in GA-treated vs. untreated patients (33).

In the present study, a simple ex vivo assay was used to measure cytokine concentration in the supernatant of PBMCs derived from the blood of RRMS patients. The data suggest that specific cytokine patterns may be associated with the identification of those who will respond to therapy with glatiramer acetate. The trend that is seen may be suggestive of cytokine patterns that could be readily measured and assist in determining GA responsiveness before GA treatment, and at an early time-point after the beginning of GA administration.

REFERENCES

1. Noseworthy J H, Lucchinetti C, Rodriguez M, Weinshenker B G. Multiple sclerosis. N Engl J Med 2000; 343:938-52.
2. Guideline on clinical investigation of medicinal products for the treatment of multiple sclerosis EMEA, London 16 September 2006.
3. Bjartmar C, Fox R J. Pathological mechanisms and disease progression of multiple sclerosis: therapeutic implications. Drugs of Today 2002; 38:17-29.
4. Fleming J O. Diagnosis and management of multiple sclerosis. 1st ed. New York: Professional communications, Inc., 2002.
5. Anderson D W, Ellenberg J H, Leventhal C M et al. Revised estimate of the prevalence of multiple sclerosis in the United States. Ann Neurol 1992; 31:333-36.
6. Compston A, Lassmann H, McDonald I. The story of multiple sclerosis. In: Compston A, Confavreux C, Lassman H, Mcdonald I, Miller D, Noseworthy J H, Smith K, Wekerle H, editors. McAlpine's Multiple Sclerosis. London: Churchill Livingstone; 2006. p. 3-68.
7. Revel M., Pharmacol. Ther., 100(1):49-62 (2003).
8. Martinelli B F, Rovaris M, Johnson K P, Miller A, Wolinsky J S, Ladkani D, Shifroni G, Comi G, Filippi M. Effects of glatiramer acetate on relapse rate and accumulated disability in multiple sclerosis: meta-analysis of three double-blind, randomized, placebo-controlled clinical trials. Mult Scler. 2003 August; 9(4):349-55.
9. Mikol D D, Barkhof F, Chang P, Coyle P K, Jeffery D R, Schwid S R, Stubinski B, Uitdehaag B M; REGARD study group. Lancet Neurol. 2008 October; 7(10):903-14. Epub 2008 Sep. 11.
10. BECOME TRIAL, Presented at the 23rd Congress of the European Committee for Treatment and Research in Multiple Sclerosis (ECTRIMS) in Prague, Czech Republic.
11. Comi G, Filippi M and Wolinsky J S. European/Canadian multi-center, double-blind randomized, placebo controlled study of the effects of glatiramer acetate on magnetic resonance imaging-measured disease activity and burden in patients with relapsing-remitting multiple sclerosis. Ann Neurol 2001; (49):290-297.
12. Fridkis H M, Aharoni R, Teitelbaum D, Arnon R, Sela M, Strominger J L. Binding of random copolymers of three amino acids to class II MHC molecules. Int. Immunol. 1999 May; 11(5):635-41.
13. Dhib-Jalbut S S, Zhan M, Johnson K P, Martin R. Glatiramer acetate reactive blood mononuclear cells respond to myelin antigens with a Th-2 biased phenotype. J Neuroimmunology 2003; 140:163-171.
14. Chen M, Gran B, Costello K, Johnson K P, Martin R, Dhib-Jalbut S. Glatiramer acetate induces a Th-2 biased response and cross-reactivity with myelin basic protein in patients with MS. Multiple Sclerosis 2001; 7:209-219.
15. Weber M S, Prod'homme T, Youssef S, Dunn S E, Rundle C D, Lee L, Patarroyo J C, Stüve O, Sobel R A, Steinman L, Zamvil S S. Type II monocytes modulate T cell-mediated central nervous sytem autoimmune disease. Nat Med (2007) 13:935-943.
16. Aharoni R, Kayhan B, Eilam R, Sela M, and Arnon R. Glatiramer acetate-specific T cells in the brain express T helper 2/3 cytokines and brain-derived neurotrophic factor in situ. PNAS August 2003; 100(24):14157-62.
17. Sarchielli P, Zaffaroni M, Floridi A, Greco L, Candeliere A, Mattioni A, Tenaglia S, Di Filippo M, Calabresi P. Production of brain-derived neurotrophic factor by mononuclear cells of patients with multiple sclerosis treated with glatiramer acetate, interferon-beta 1a, and high doses of immunoglobulins. Mult Scler 2007 April; 13(3):313-31. Epub 2007 Jan. 29.
18. Bornstein, M B, Miller, A, Slagle, S, et al. A pilot trial of Cop 1 in exacerbating remitting multiple sclerosis. *New Eng J Med* 1987; 317: 408-14.
19. Comi, G, Fillippi, M, Wolinsky, J S, et al. European/Canadian multicenter, double-blind, randomized, placebo-controlled study of the effects of glatiramer acetate on magnetic resonance imagine-measured disease activity and burden in patients with relapsing multiple sclerosis. *Ann Neurol* 2001; 49: 290-7.
20. Johnson, K P, Brooks, B R, Cohen, J A, et al. Extended use of glatiramer acetate (Copaxone) is well tolerated and maintains its clinical effect on multiple sclerosis relapse rate and degree of disability. *Neurology* 1998; 50:701-8.
21. Bornstein, M B, Miller, A, Slagle, S, et al. A placebo-controlled, double-blind, randomized, two-center, pilot trial of Cop-1 in chronic progressive multiple sclerosis. *Neurology* 1991; 41: 533-39.
22. Wolinsky, J S, Narayana, P A, O'Conner, P, et al. Glatiramer acetate in primary progressive multiple sclerosis: Results of a multinational, multicenter, double-blind, placebo-controlled trial. *Ann Neurol* 2007; 61:14-24.
23. Comi G, Filippi M, Treatment with glatiramer acetate delays conversion to clinically definite multiple sclerosis (CDMS) in patients with clinically isolated syndromes (CIS). *Neurology* 2008; 71 (2): 153.
24. Tselis, A, Khan, O, Lisak, R P, Glatiramer acetate in the treatment of multiple sclerosis. *Neuropsychiatric Dis Treat* 2007; 3(2):259-67.
25. Wolinsky, J S, The use of glatiramer acetate in the treatment of multiple sclerosis. *Adv Neurol* 2006; 273-92.
26. Comi G, Cohen J A, Filippi M, Results from a phase III, one-year, randomized, double-blind, parallel-group, dose-comparison study with glatiramer acetate in relapsing-remitting multiple sclerosis. *Mult Scler* 2008; 14(suppl 1):S299.
27. Comi G, Filippi M. Presented at: 60th Annual Meeting of the American Academy of Neurology: April 12-19; Chicago, Ill. Abstract LBS.003.
28. Johnson D, Hafler D A, Fallis R J, Lees M B, Brady R O, Quarles R H, Weiner H L., "Cell-mediated immunity to myelin-associated glycoprotein, proteolipid protein, and myelin basic protein in multiple sclerosis.", *J. Neuroimmunol.* 1986 November; 13 (1):99-108.
29. Brex P A et al., "A longitudinal study of abnormalities on MRI and disability from multiple sclerosis", *N Engl J Med* 2002 Jan. 17, 346(3):158-64.
30. Frohman E M et al., "The utility of MRI in suspected MS: report of the Therapeutics and Technology Assessment Subcommittee of the American Academy of Neurology", *Neurology,* 2003, Sep. 9, 61 (5): 602-11.
31. Poser C M. et al. New diagnostic criteria for multiple sclerosis: Guidelines for research protocols. Ann. Neurol., 13(3): 227-31, 1983
32. Neurostatus, slightly modified from J. F. Kurtzke Neurology 1983:33, 1444-52; L. Kappos, Dept. of Neurology, University Hospital, CH-4031/Basel, Switzerland.
33. Farina C, Then Bergh F, Albrecht H, Meinl E, Yassouridis A, Neuhaus O, Hohlfeld R. Treatment of multiple sclerosis with Copaxone (COP): Elispot assay detects COP-induced interleukin-4 and interferon-gamma response in blood cells. Brain. 2001 April; 124(Pt 4):705-19.

What is claimed is:

1. A method for treating a human subject afflicted with multiple sclerosis or a single clinical attack consistent with multiple sclerosis with a pharmaceutical composition comprising glatiramer acetate and a pharmaceutically acceptable carrier, comprising the steps of:
   a) determining whether the human subject is a glatiramer acetate responder by evaluating IFN-γ concentration in a supernatant of PBMCs derived from the human subject's blood, which human subject can be identified as a glatiramer acetate responder by steps comprising,
      (i) purifying PBMCs from the subject's blood and then cryopreserving the PBMCs,
      (ii) thawing and then culturing the cryopreserved PBMCs overnight in culture medium supplemented with 5% human serum,
      (iii) stimulating about 40,000 of said cultured PBMCs with 1 mg/ml PMA and 5 mg/ml ionomycin in a final volume of 200 microliters for 6 hours, and
      (iv) identifying the human subject as a glatiramer acetate responder if IFN-γ concentration of a supernatant of PBMCs after step (iii) is greater than or equal to 6000 pg/ml; and
   b) administering the pharmaceutical composition comprising glatiramer acetate and a pharmaceutically acceptable carrier to the human subject only if the human subject is identified as a glatiramer acetate responder,
   wherein the human subject is a naive patient or wherein the human subject has been previously administered a multiple sclerosis drug other than glatiramer acetate.

2. The method of claim 1, wherein administering the pharmaceutical composition comprising glatiramer acetate and a pharmaceutically acceptable carrier comprises administering to the human subject three subcutaneous injections of the pharmaceutical composition over a period of seven days with at least one day between every subcutaneous injection.

3. The method of claim 1, wherein the pharmaceutical composition is a unit dose of a 0.5 ml aqueous solution comprising 20 mg of glatiramer acetate.

4. The method of claim 1, wherein if the human subject is identified as a glatiramer acetate responder, the human subject is thereafter administered the pharmaceutical composition comprising glatiramer acetate and a pharmaceutically acceptable carrier as monotherapy.

5. The method of claim 1, wherein if the human subject is not identified as a glatiramer acetate responder, the human subject is thereafter administered a multiple sclerosis drug which is not glatiramer acetate.

6. The method of claim 1, wherein the human subject is a naive patient.

7. The method of claim 1, further comprising in step (iv) identifying the human subject as a glatiramer acetate responder based on IL-17 concentration, TNF-α concentration, IL-2 concentration, or a combination thereof, of a supernatant of the PBMCs after step (iii).

8. The method of claim 1, comprising in step (iv) identifying the human subject as a glatiramer acetate responder based on IFN-γ concentration, IL-17 concentration, TNF-α concentration and IL-2 concentration of a supernatant of the PBMCs after step (iii).

9. A method of predicting clinical responsiveness to glatiramer acetate therapy in a human subject afflicted with multiple sclerosis or a single clinical attack consistent with multiple sclerosis, the method comprising evaluating IFN-γ concentration in a supernatant of PBMCs derived from the human subject's blood, which human subject can be identified as a glatiramer acetate responder by steps comprising,
   (i) purifying PBMCs from the subject's blood and then cryopreserving the PBMCs,
   (ii) thawing and then culturing the cryopreserved PBMCs overnight in culture medium supplemented with 5% human serum,
   (iii) stimulating about 40,000 of said cultured PBMCs with 1 mg/ml PMA and 5 mg/ml ionomycin in a final volume of 200 microliters for 6 hours, and (iv) identifying the human subject as a glatiramer acetate responder if IFN-γ concentration of a supernatant of PBMCs after step (iii) is greater than or equal to 6000pg/ml, to thereby predict clinical responsiveness to glatiramer acetate, wherein the human subject is a naive patient or wherein the human subject has been previously administered a multiple sclerosis drug other than glatiramer acetate.

10. The method of claim 9, wherein the glatiramer acetate therapy comprises administering to the human subject three subcutaneous injections of a pharmaceutical composition comprising glatiramer acetate and a pharmaceutically acceptable carrier over a period of seven days with at least one day between every subcutaneous injection.

11. The method of claim 9, further comprising in step (iv) identifying the human subject as a glatiramer acetate responder based on IL-17 concentration, TNF-α concentration, IL-2 concentration, or a combination thereof, of a supernatant of the PBMCs after step (iii).

12. The method of claim 9, comprising in step (iv) identifying the human subject as a glatiramer acetate responder based on IFN-γ concentration, IL-17 concentration, TNF-α concentration and IL-2 concentration of a supernatant of the PBMCs after step (iii).

13. The method of claim 9, wherein the human subject is a naive patient.

14. A method for treating a human subject afflicted with multiple sclerosis or a single clinical attack consistent with multiple sclerosis comprising the steps of:
 a) administering to the human subject a therapeutic amount of a pharmaceutical composition comprising glatiramer acetate and a pharmaceutically acceptable carrier, wherein the human subject is a naive patient or wherein the human subject has been previously administered a multiple sclerosis drug other than glatiramer acetate;
 b) evaluating IFN-γ concentration in a supernatant of PBMCs derived from the human subject's blood, which human subject can be identified as a glatiramer acetate responder by steps comprising,
  (i) purifying PBMCs from the subject's blood and then cryopreserving the PBMCs,
  (ii) thawing and then culturing the cryopreserved PBMCs overnight in culture medium supplemented with 5% human serum,
  (iii) stimulating about 40,000 of said cultured PBMCs with 1 mg/ml PMA and 5 mg/ml ionomycin in a final volume of 200 microliters for 6 hours, and
  (iv) identifying the human subject as a glatiramer acetate responder if IFN-γ concentration of a supernatant of PBMCs after step (iii) is greater than or equal to 6000pg/ml; and
 c) continuing administration of the pharmaceutical composition if the human subject is identified as a glatiramer acetate responder, or modifying the administration of the pharmaceutical composition to the human subject if the human subject is not identified as a glatiramer acetate responder.

15. The method of claim 14, wherein administering to the human subject a therapeutic amount of a pharmaceutical composition comprising glatiramer acetate and a pharmaceutically acceptable carrier comprises administering to the human subject three subcutaneous injections of the pharmaceutical composition over a period of seven days with at least one day between every subcutaneous injection.

16. The method of claim 14, wherein the IFN-γ concentration is observed at 2 months after the first administration of glatiramer acetate.

17. The method of claim 14, further comprising in step (iv) identifying the human subject as a glatiramer acetate responder based on IL-17 concentration, TNF-α concentration, IL-2 concentration, or a combination thereof, of a supernatant of the PBMCs after step (iii).

18. The method of claim 14, comprising in step (iv) identifying the human subject as a glatiramer acetate responder based on IFN-γ concentration, IL-17 concentration, TNF-α concentration and IL-2 concentration of a supernatant of the PBMCs after step (iii).

19. The method of claim 14, wherein the human subject is a naive patient.

* * * * *